United States Patent
Seymen et al.

(10) Patent No.: US 11,389,240 B2
(45) Date of Patent: Jul. 19, 2022

(54) FIBER PROBE THAT EMITS A PAIR OF RING BEAMS FOR LASER ABLATION

(71) Applicants: E-A TEKNOLOJI BIYOMEDICAL CIHAZLAR DIJITAL VE OPTIK SISTEMLER NANOTEKNOLOJI AR-GE ITH. IHR. TAAH. SAN. VE TIC. LTD. STI., Ankara (TR); VAMET MEDIKAL SAGLIK URUNLERI VE HIZMETLERI AKARYAKIT ENERJI MADENCILIK GIDA ELEKTRONIK SANAYI VE TICARET LIMITED SIRKETI, Ankara (TR)

(72) Inventors: Ali Aytac Seymen, Ankara (TR); Bulend Ortac, Ankara (TR); Erol Ozgur, Ankara (TR)

(*) Notice: Subject to any disclaimer, the term of this patent is extended or adjusted under 35 U.S.C. 154(b) by 105 days.

(21) Appl. No.: 16/649,752

(22) PCT Filed: Sep. 21, 2018

(86) PCT No.: PCT/TR2018/050516
§ 371 (c)(1),
(2) Date: Mar. 23, 2020

(87) PCT Pub. No.: WO2019/059870
PCT Pub. Date: Mar. 28, 2019

(65) Prior Publication Data
US 2020/0237439 A1 Jul. 30, 2020

(51) Int. Cl.
*A61B 18/20* (2006.01)
*A61B 18/22* (2006.01)
(Continued)

(52) U.S. Cl.
CPC .... *A61B 18/22* (2013.01); *A61B 2017/00526* (2013.01); *A61B 2017/00783* (2013.01);
(Continued)

(58) Field of Classification Search
CPC .............................. A61B 18/20; A61F 9/008
See application file for complete search history.

(56) References Cited

U.S. PATENT DOCUMENTS 5,078,711 A * 1/1992 Kakami ................. A61B 18/22
606/16
2002/0045811 A1 4/2002 Kittrell et al.
(Continued)

FOREIGN PATENT DOCUMENTS

| KR | 20130114403 A | 10/2013 |
|---|---|---|
| WO | 2011085299 A3 | 7/2011 |
| WO | 2012047309 A1 | 4/2012 |

OTHER PUBLICATIONS

International Search Report for corresponding PCT/TR2018/050516.
Written Opinion of the ISA for corresponding PCT/TR2018/050516.

*Primary Examiner* — Lynsey C Eiseman
(74) *Attorney, Agent, or Firm* — Egbert, McDaniel & Swartz, PLLC

(57) ABSTRACT

A laser ablation device which, an emitting double ring beam at the tip, is used in treatment, without permanent damage and scar, of natural diseases like venous insufficiency, of subsequently-formed diseases like fistula or of hemorrhoids formed as damaging of the vein. The device includes a fiber probe with two different conical angled surfaces where the rays guided through inside the fiber are reflected at the fiber tip via a first conical shaped-end formed at a first specific angle at the fiber's tip and a second conical shaped-end (Continued)

formed at different second specific angle by starting from a certain portion of the first conical shaped-end.

2 Claims, 8 Drawing Sheets

(51) Int. Cl.
    *A61B 17/00*         (2006.01)
    *A61B 18/00*         (2006.01)

(52) U.S. Cl.
    CPC .............. *A61B 2018/00404* (2013.01); *A61B 2018/00577* (2013.01); *A61B 2018/208* (2013.01); *A61B 2018/2272* (2013.01)

(56) References Cited

U.S. PATENT DOCUMENTS

| | | | | |
|---|---|---|---|---|
| 2007/0263975 | A1* | 11/2007 | Boutoussov | B23K 26/073 385/146 |
| 2008/0247714 | A1* | 10/2008 | Nakamura | G02B 6/2551 385/96 |
| 2011/0282330 | A1 | 11/2011 | Harschack et al. | |

* cited by examiner

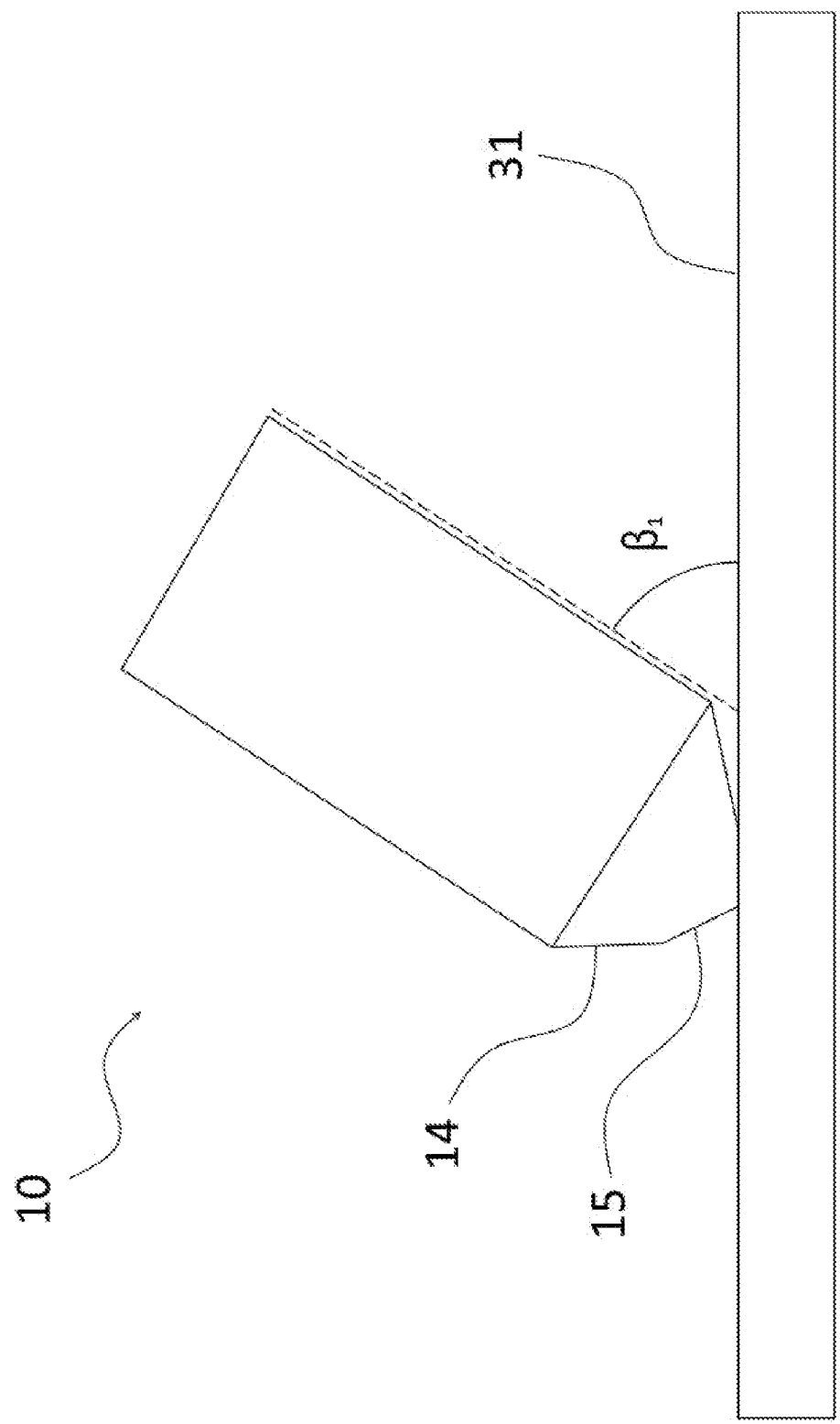

FIBER PROBE THAT EMITS A PAIR OF RING BEAMS FOR LASER ABLATION

TECHNICAL FIELD

The invention relates to a fiber probe that emits a pair of ring beams by changing its tip geometry, and an achieving method therefor.

More particularly, the present invention relates to a fiber probe obtained by forming two-angled conical end geometry on a single fiber end, by using a polishing method, in which the laser beam guided along the fiber to the fiber end is deflected into two circular rings.

The invention also relates to a laser ablation device which, emitting double ring beam at the tip, is used in treatment, without permanent damage and scar, of natural diseases like venous insufficiency, of subsequently-formed diseases like fistula or of hemorrhoids formed as damaging of vein in short distance and etc., also capable of counter-beaming in specific applications like hemorrhoids.

PRIOR ART

The valves within the veins are open when the blood flows towards the heart. When going in the opposite direction, the valves help to the normal motion of the blood by closing. In the patients having venous insufficiency, these valves do not function properly (in a healthy way). Therefore, accumulation occurs within veins. Varicose veins caused due to venous insufficiency are frequently encountered in the society. In the treatment of varicose veins which is a health problem affecting life standards adversely, a number of methods have been used.

Pressure socks designed as special for varicose veins can be used in treatment of varicose veins caused due to venous insufficiency. In this way, growth of varicose veins is prevented. However, in this case the patient will need to use a drug that regulates the blood pressure for a long time, so this method is not useful for the patient and can't be used in the treatment of advanced varicose veins.

Vein stripping method is a surgical method that requires anesthesia before the operation. Also, the recovery period is long. In sclerotherapy treatment, salt water or medication is injected into the vessels suffering from venous insufficiency. This method does not require incision and anesthesia before operation but it is a painful method.

Finally, various surgical methods like vein removal, bypass (replacement with non-congested vein) are disadvantageous because they require anesthesia, surgical incision, and they could leave pain, infection risk of incision area, wound and permanent damage. Classical treatments could cause many side effects. Recently, laser devices have been frequently used in the treatment of venous insufficiency.

In addition to varicose veins, hemorrhoids, fistulas and similar diseases are also commonly encountered. 80% of people faces hemorrhoids at least once in their lives. Hemorrhoids, as in varicose veins, occur as a result of vein enlargement in the perianal region. If the venous pressure within the hemorrhoids tissue increases, this tissue swells and begins to prolapse. As a result, it becomes a disease. The fistula is a disease which causes a rectal discharge around the rectum by bringing a gap between the skin and the intestines. As well as in the treatment of diseases such as hemorrhoids, fistulas and varicose veins, laser ablation devices are also preferred in the treatment of thyroid nodules and the treatment of tumors in the organs such as prostate, breast and liver because they do not cause any cuts, wounds and tissue loss and their healing (recovery) period is shorter.

Optical fibers have been frequently used in the health sector for lithotripsy, venous insufficiency and photo thermal tissue ablation. Laser ablation is a treatment method based on the treatment of damaged vessel within the vessel by applying appropriate laser energy by inserting a thin structure into the vein instead of removing the damaged vessels by surgery. The operation/implementation and recovery time of this treatment is much shorter than the other treatment methods. The patient can return immediately to his/her daily activities. It has a higher success rate than surgery and other classical methods and has less probability to recur.

Optical fiber cables are glass or plastic structures in which beams can easily pass through. Optical fibers supported by diagonal modes and spreading lines are called multimode fiber optics. Single-mode fibers are fibers supported by a single mode. It is difficult and complicated to make addition to optical fiber cables. The fiber ends to be joined must be carefully cut and then joined by melting it or mechanically.

Since the diameter of the optical fibers is flexible and compatible with the human tissue, they transmit the desired energy. There are three types of laser beams that are used for medical purposes: bare, radial, and side-firings. The bare optical fiber emits laser light in the same direction with the optical fiber that the side-pushing fiber vertically transmits the laser beam to its fiber axis so, it forms a circular beam. Radial fibers emit laser light homogeneously at 360 degrees so, they form a circular beam. Generally, radial fibers are used in the elimination of venous insufficiency. In the treatment of venous insufficiency, ring-shaped beams are the most ideal laser beam shape. The main reason to use the ring type beam is that the ring type beams transmit less ray towards the vessel walls. Double-ring optical fibers have advantages of, such as, reduction of intensity distribution and of temperature increase for each ring. While the first ring heats the vessel wall, second ring removes the heated surface. Although the advantages of the double ring over venous are known, there is little information about the production technique.

The document WO2011085299 mentions a radiotherapy method under fat tissue by means of a radiation energy source. The methods described as radiation-assisted tissue healing includes insertion of a portion of a device or of a part under the skin that will be treated, radiation transmission/ exposure, and movement of device within the tissue area to reach all damaged-tissue. The device performing subcutaneous (under the skin) radiation therapy includes a portion that can be inserted under the skin and a handpiece that can be held and manipulated outside the body. In this preferred embodiment, the handpiece contains a hollow cannula containing at least one channel for the treatment and/or irrigation of the fat tissue, and a light guiding device in the body-wall region for the purpose of treating and liquefying of the fat tissue. A wide variety of fiber-optic configurations are available. For example, side-emitting, conical, radial emitting, drop-shaped, reflective lids can be used. Device contains at least one radiation source added to device part that permanently or removably attached to the handpiece. However, it is a device related to the removal of fat tissue, not developed to venous insufficiency and similar diseases.

At the document KR20130114403, waste material in the blood vessel can be melted by means of a fiber optic device with ring-shaped beam exit by adding a small optical system (a convex and concave shaped mirror or an aluminum covered attachment part added to the optical fiber end) to the existing optical fiber. However, in this patent document, it is not mentioned about two rings at specific diameters obtained by polishing method with specific angles, the rings in mentioned treatment method are obtained with an additional system added to the fiber optic tip.

According to patent document WO2012047309, this device consists of an optical fiber that includes two or more radiating parts in the distal region to provide 360° radial emission to vessel. According to the patent document, the device has two beam spreading zones. The beam propagation direction is determined by the angle of the fiber's conical parts. The fiber may be fused with the truncated cone. When it is not fused, the space inside can be filled with glue or liquid. The lateral surface of the fiber can be fused or glued with a glass dome. By combining (addition) two optical fibers formed at two different angles, desired reflection angles are obtained. Venous insufficiency and similar diseases are treated thanks to two or more ring-shaped beams having a diameter proportional to the reflection angle obtained by this method. However, the technique used in the production of this device has disadvantage when considered as economically.

As a result, due to that the production difficulties of the prior art solutions increase the final product cost and prevent the solution to be commonly used, the require for a dual ring laser device which can be manufactured easier and at lower cost lets the present invention to come up.

Objectives and Short Description of the Invention

The objective of invention is to present a laser probe which, emitting energy-dual ring beams around 15 W from an optical fiber's fiber tip formed by polishing and sanding method, is used treatment of diseases like venous insufficiency, of subsequently-formed diseases like fistula or of hemorrhoids formed as damaging of vein in short distance and etc., which does not require anesthesia or any preparation before operation, and which allows a treatment without permanent damage and scar, and to present a production method therefore.

Another objective of the invention is to present a fiber probe with two different conical angled surfaces where the rays guided through inside the fiber are reflected at fiber tip via a first conical shaped-end formed at a first specific angle at fiber's tip and a second conical shaped-end formed at different specific angle by starting from a certain portion of the first conical shaped-end.

Another objective of the invention is to present a truncated fiber end containing a flattened portion through, where laser beam guided through inside the fiber along the fiber axis to fiber end is guided along fiber axis to outside for allowing the laser beam to be used as counter strike at a certain energy level in addition to lateral strike.

Another objective of the invention is to present a laser ablation device-production method containing placing the untreated fiber surface on the first film surface that is used in the polishing system with a specific initial positioning angle to give a first form to the fiber end, taking the first tapered shape in this first positioning direction, placing the fiber end which completes first procedure then takes tapered-shape, on the second film surface, machining the second form until certain portion of first region with a certain second positioning angle, thereby forming the second region at the fiber end.

DESCRIPTION OF THE FIGURES

In FIG. 2a, the placement of the optical fiber to a polishing machine at a certain angle to obtain a dual ring laser output end is shown. In FIG. 2c, the process of giving the final shape or final form of the optical fiber end by giving a second angle to the end portion in which an intermediate form is obtained with first angle is shown.

In FIG. 6a, the power differences of the double ring beams are compared with each other for a=100.

In FIG. 7a, it is shown that the inner ring diameter decreases with the decrease of the angle θ, in other word, it moves inward away from the outer ring.

REFERENCE NUMERALS

Figure 1:
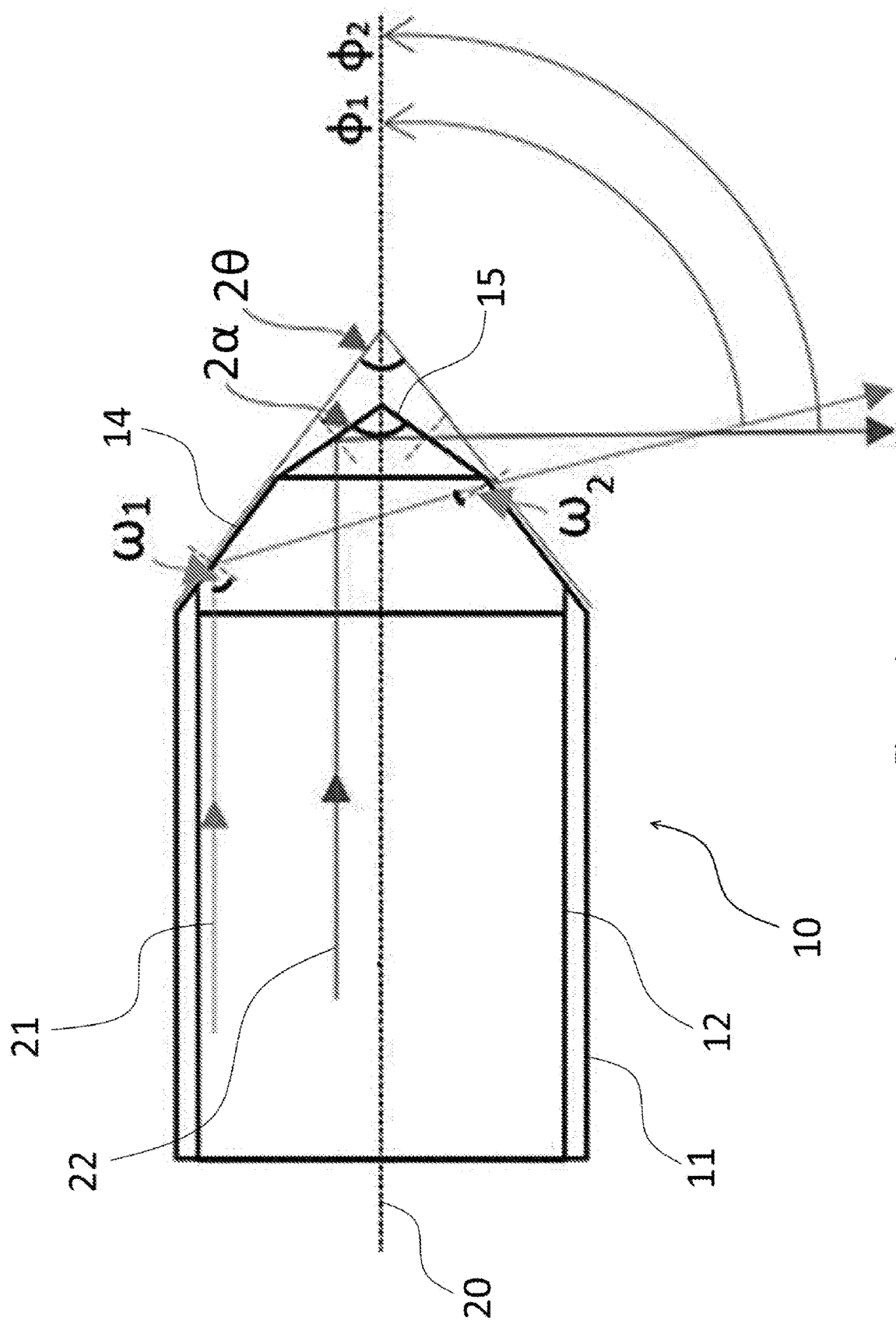
In FIG. 1, the end portion of the present fiber probe emitting a double ring laser beam and the paths of mentioned double ring laser beam obtained by the present inventive method are given.

10. Fiber tip
11. Cladding
12. Core
13. Untreated fiber surface
14. First section
15. Second section
20. Fiber axis
21. First beam path
22. Second beam path
30. First film surface
31. Second film surface
40. Probe
41. Detector
42. Measurement axis
43. Truncated fiber tip
44. Conical fiber tip
45. Glass body
θ. First angle
α. Second angle
$\omega_1$. First reflection angle
$\omega_2$. First refraction angle
$\varphi_1$. First ring angle
$\varphi_2$. Second ring angle
$\alpha_1$. First positioning angle)
$\beta_1$. Second positioning angle a. Vertical distance between the first section start and fiber axis
b. Vertical distance between the second section start and fiber axis
x. distance between the first section and second section
y. distance between the second section and fiber tip

DETAILED DESCRIPTION OF THE INVENTION

The invention relates to a laser probe (40) which, emitting energy-dual ring beams from an optical fiber's fiber tip (10) formed by polishing and sanding method, is used treatment of natural diseases like venous insufficiency, of subsequently-formed diseases like fistula or of hemorrhoids formed as damaging of vein in short distance and etc., which does not require anesthesia or any preparation before operation, and which allows a treatment without permanent damage and scar, and to a production method therefore.

Circular beam deflection could be obtained by means of conical shaped fiber optic devices. Deflection angle and conical angle could be calculated by using Snell law and ray tracing. There are three basic scenarios for light deflection from a conical shaped optical fiber probe (40). In the first scenario, the incoming rays reflect from the first boundary, and when $\theta_{cone} < \pi - 2\theta_{cone\text{-}air}$, they refract toward out of the optical fiber. The critical angle $\theta_{cone\text{-}air}$ which is equal to 43.3° when the tip angle is in the range $\theta_{cone} < \pi - 2\theta_{cone\text{-}air}$ to obtain the side deflection calculated by $\theta_{cone\text{-}air} = \sin^{-1}(n_{air}/n_{core})$ to provide the total internal reflection (TIR) from the first boundary.

The reflected beam proceeds toward the second cone-air boundary, and the angle between surface normal and incoming ray is $\omega_r$, and it is calculated by using $\omega_2 = |90 + \omega_1 - \theta_{cone}|$ from geometry. The laser beam refracts at this boundary; and the refraction angle is calculated by using $\theta_{refracted} \sin^{-1}((n_{core}/n_{air})\sin \omega_2)$. Using this calculation, the deflection angle is transformed into the following equation:

$$\varphi = \frac{180 - \theta}{2} - \sin^{-1}\left(\frac{ncore}{n_{air}}\sin\omega_2\right)$$

In the second scenario, the incoming beams reflect back into the optical fiber. If the fiber end angle is in the range $\theta_{refracted} = \sin^{-1}((n_{core}/n_{air})\sin \omega_2)$, deflection is not expected. In the third scenario; when $\theta\_cone < \pi - 2\theta\_(core\text{-}air)$, the coming beams directly refract from the first boundary. For this case the following equation can be written:

$$\varphi = \sin^{-1}\left(\frac{n_{core}}{n_{air}}\sin\omega_1\right) - \omega_1$$

In the method of the invention, 56° and 72° tip angles are used in the range $\theta_{cone} < \pi - 2\theta_{core\text{-}air}$. In FIG. 1, the paths of the double ring laser beam obtained from the fiber tip (10) that is formed by the method of the invention are given. Mentioned fiber tip (10) is obtained by treating a tip of standard multimode optical fiber of 600 μm, 630 μm and 1040 μm. However, any multi-mode fiber that can be specially produced for the purpose and application could be also used. The fiber structure essentially comprises a cladding (11) and a core (12). In FIG. 1, how the double ring is obtained is explained by using representative two beams. Two-angled section is obtained on a single fiber tip (10) by treating the untreated fiber surface (13) with a polishing technique as shown in FIG. 2. In FIG. 1, the second section (15) is angled to fiber axis (20) with second angle (a) while the first section (14) is angled with first angle (θ). The angle of the first beam path (21) to the first section (14) forms the first reflection angle ($\omega_1$). The angle formed by coming of incoming angle from the first beam path (21) to the bottom of the first section (14) by reflecting from the first section (14) forms the first refraction angle ($\omega_2$). The angle formed between the first beam path (21) reflected by the first reflection angle ($\omega_1$) and the fiber axis (20) forms the first ring angle ($\varphi_1$) and the angle formed between the second beam path (22)'s reflection that comes from the second section (15) and the fiber axis (20) forms the second ring angle ($\varphi_2$.)

In FIG. 1, how the double ring beam is obtained from the fiber tip (10) of the present fiber probe (40) is described by means of representative beam paths. Here, the first beam path (21) represents modes which are away from the fiber axis (20), proceed near the cladding (11) and refract in the first section (14). The second beam path (22) shows the modes proceeding closer to the fiber core (12) and refracting in the second section (15). Accordingly, when observed from fiber tip (10), the incoming beams to the first section (14) result in a broad ring formation by refracting at a wider angle. The incoming beams to the second section (15) form a ring with smaller diameter at the same fiber axis (20), around the fiber and interior of first ring by refracting at a narrower angle according to the first section (14). When the value of first angle (θ) formed between the first section (14) and the fiber axis (20) is decreased, the inner ring gets smaller, when the value of first angle (θ) is increased, the inner ring gets bigger. When the value of second angle (α) formed between the second section (15) and the fiber axis (20) is increased, the outer ring gets bigger, when the value of second angle (α) is decreased, the outer ring gets smaller.

Figure 2A:
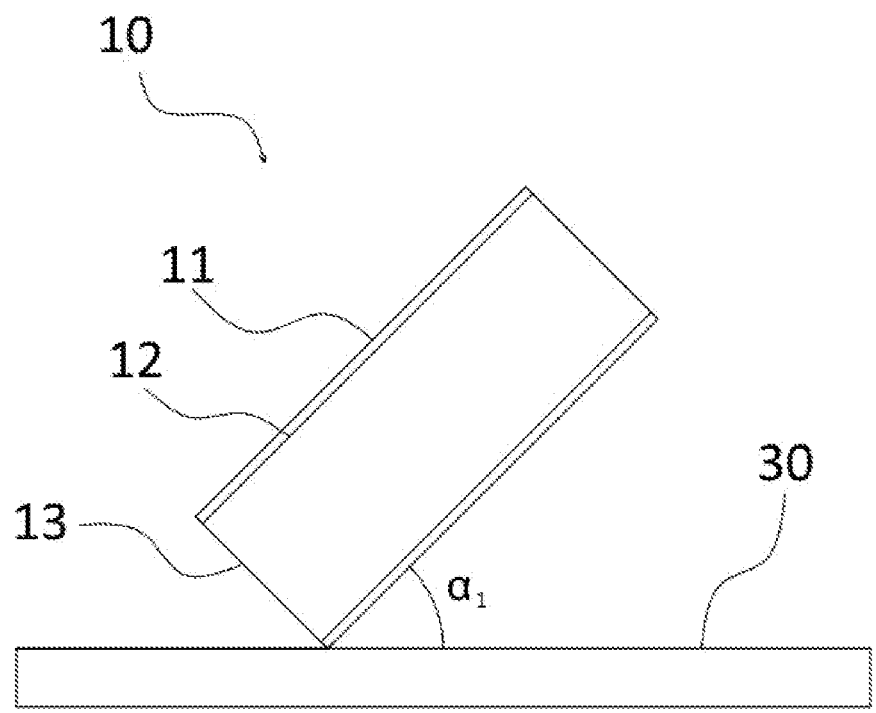
In FIGS. 2a, b, and c, operational steps for obtaining a dual ring laser output end by the present method are shown.
Figure 2B:
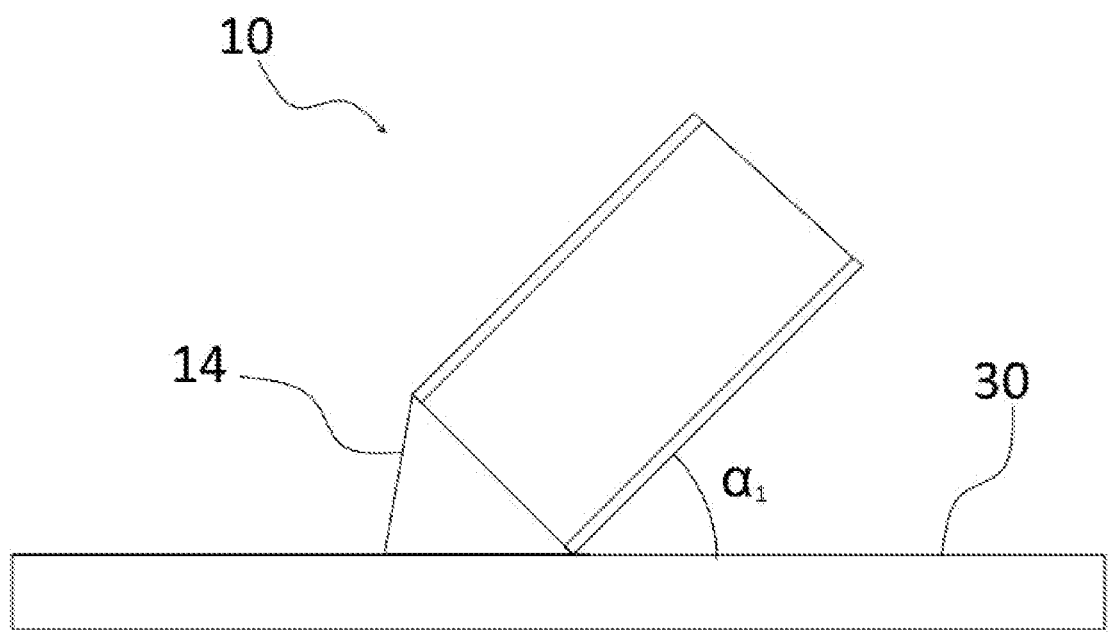
In FIG. 2b, formation of an intermediate form at the end portion and of a first shape of the end portion by processing the optical fiber with a polishing tool at a certain angle are described.
Figure 5:
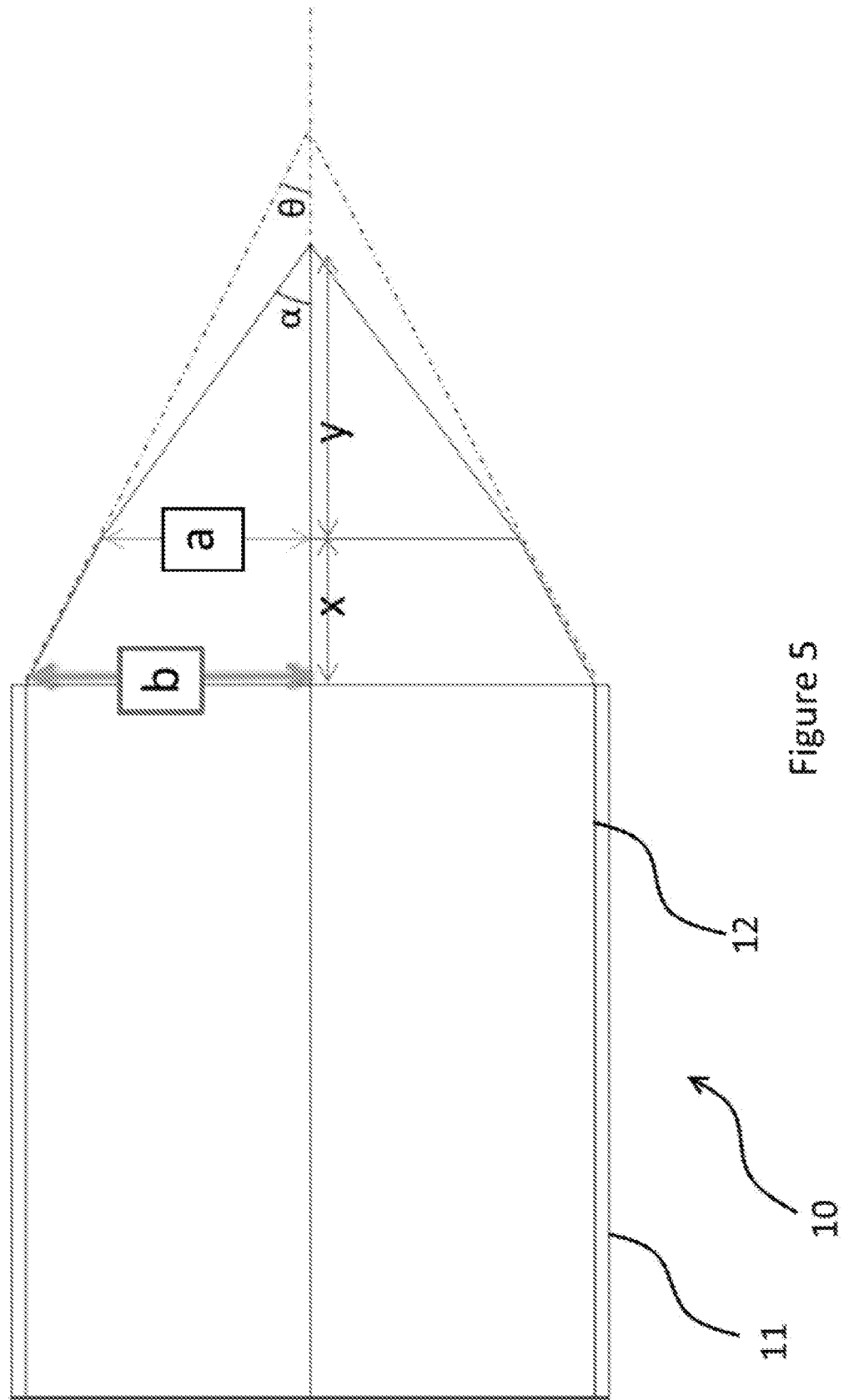
In FIG. 5, the fiber end geometry parameters affecting the physical properties of the laser beams obtained by the present fiber probe are depicted.

As seen in FIG. 2a, it is described that the first section (14) at a certain angle and then the second section (15) at a second angle (α) as in FIG. 2b are formed by treating the flat-cut untreated fiber surface (13) by using sanding and polishing technique. Firstly, to give the first form to the fiber tip (10), the untreated fiber surface (13) is placed with a certain initial positioning angle ($\propto_1$) on the first film surface (30) which is used in the polishing system, and the fiber tip (10) takes its first conical shape at this first positioning angle ($\propto_1$), and mentioned first angle (θ) at the tip is obtained. Then, as shown in FIG. 2c, the fiber tip (10) which is completed the first step and takes conical shape is placed on the second film surface (31). At this time, the end portion is treated until a specific portion of the first section (14) to the second film surface (31) with a certain second positioning angle $\beta_1$) and so that the second section (15) is formed at the fiber tip (10). The beginning of the second section (15) is in the middle or near the middle of the first section (14). The fiber end geometry parameters affecting the physical properties of the obtained double ring laser beam are shown in FIG. 5. Each parameter mentioned here specifies the thicknesses and diameters of the rings in the double ring laser, and thus their relative powers to each other. These include the distance in the horizontal axis between the first section (14) and the second section (15), the vertical distance of the angle change points forming each section to the fiber axis (20), and the angles that each section makes with the fiber axis (20).

Figure 3:
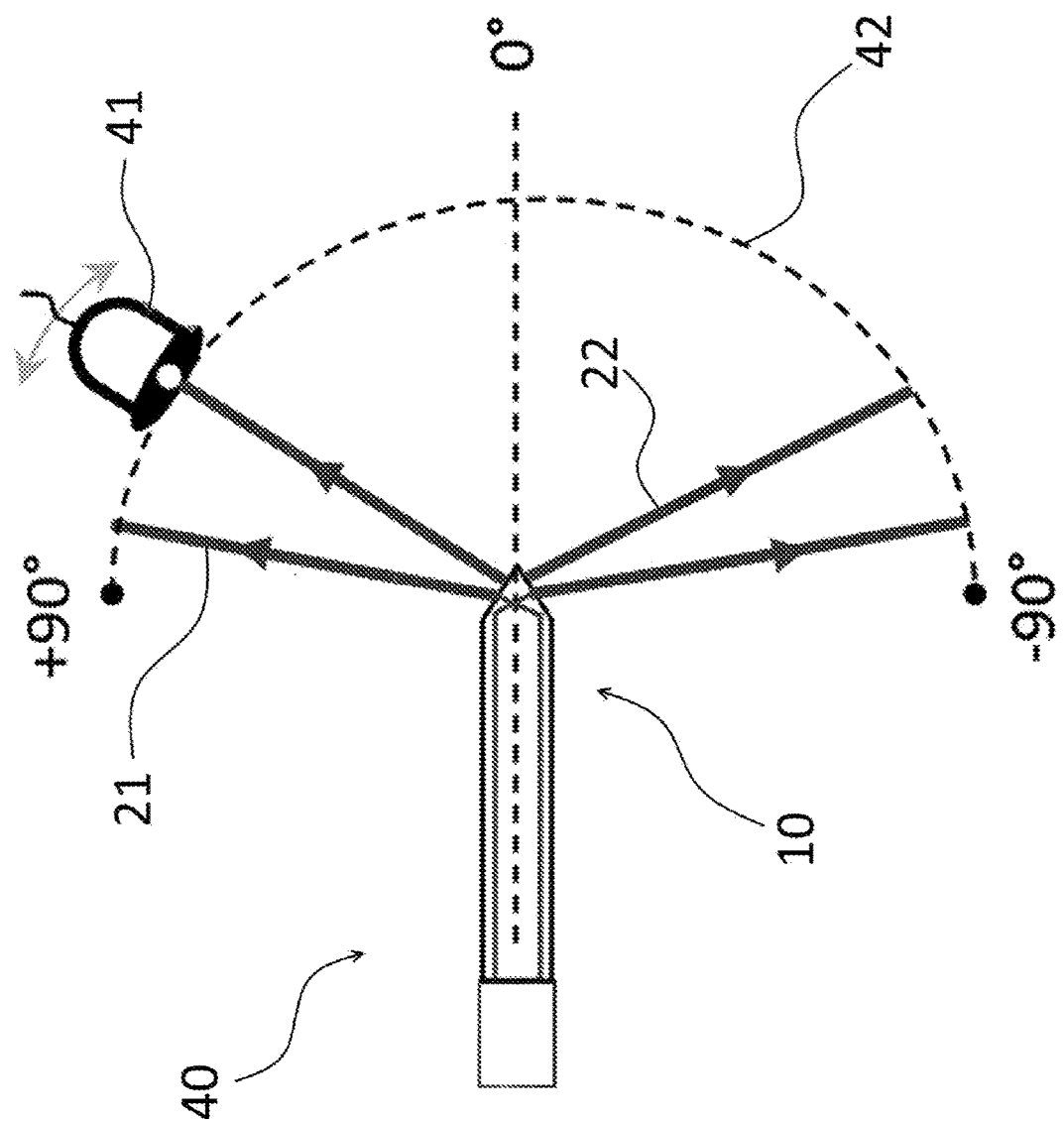
In FIG. 3, obtaining the present double ring laser by means of a multi-mode optical fiber and measuring the structure of double ring laser beam by means of a sensor are depicted.

In FIG. 3, obtaining dual ring laser beam by means of a multimode optical fiber and measuring the double ring laser beam structure by means of a sensor or detector (41) are depicted. This means that the wavelength is suitable for obtaining the ultimate laser beam required for treatment. However, with the present probe (40), it is possible to obtain double ring lasers with laser beams at different wavelengths to use in different fields. The optical fiber used in the method of the present invention is multimode. By applying sanding and polishing method to the untreated fiber surface (13) located at the end portion of the optical fiber probe (40), two portions through which two different laser rings are formed around the fiber tip (10), namely the first section (14) and the second section (15), are formed. With the aid of a detector (41) attached to the end of the optical fiber probe (40), the power data at each angle can be read on the measurement axis (42) and a circular path ranging from +100 to −100 is scanned. In FIGS. 6a, 6b, 6c and 7a and 7b, views regarding to the measurements obtained from the end portion of the present fiber probe (40) by means of mentioned detector (41) and to changes in the double ring laser obtained according to the parameters given in FIG. 5 are shown.

Since the end of the optical fibers (40) is treated in two different angles step by step, radial light output is performed at two different angles, unlike the standard radial output optical fibers (40). Mentioned two-separate ring-shaped light outlets allow the power of the optical fiber (40) to spread homogeneously across the vessel during treatment. Radial light outputs are obtained through the second sanding and polishing steps, which are done in a way that is equal and controlled. The longer the second sanding and polishing stage is performed and the lower the surface roughness at the appropriate time parameters, the greater the energy density of the outer radial ring will also increase. The most important innovation in this method is that said light output is obtained by sanding and polishing the single piece optical fiber probe (40) at two different angles. Thanks to this feature, cost advantage is provided, as well as easy production.

Figure 4A:
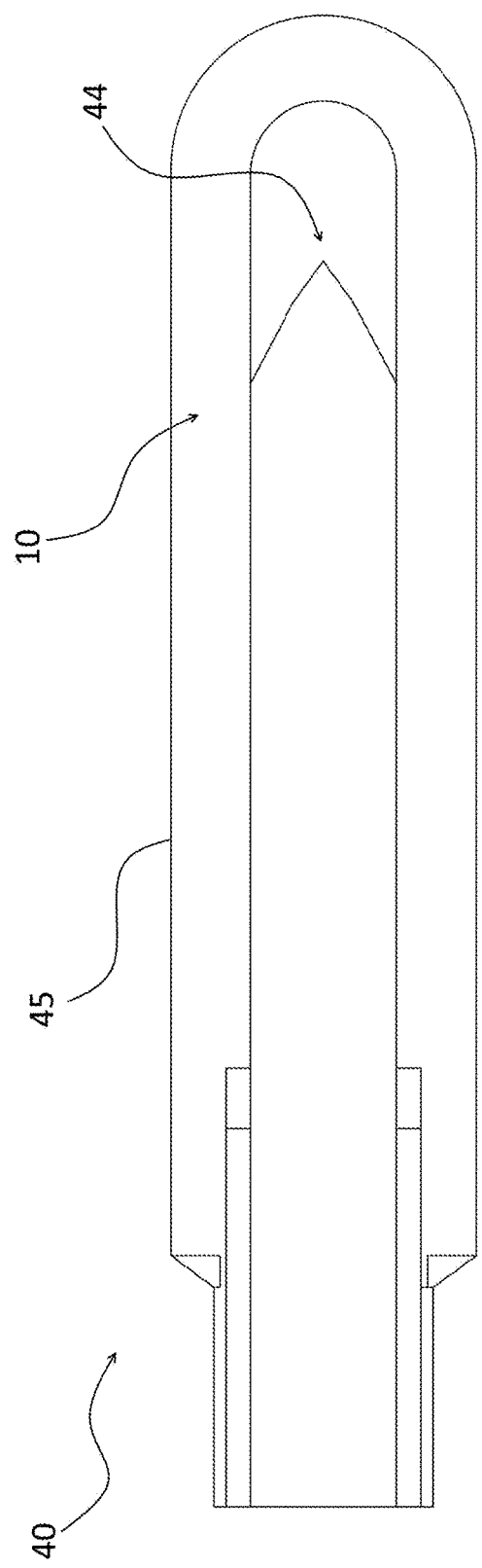
In FIG. 4a, a fiber probe which emits double ring radiation for laser ablation and which's tip is sharp to provide just lateral strike is shown.
Figure 4B:
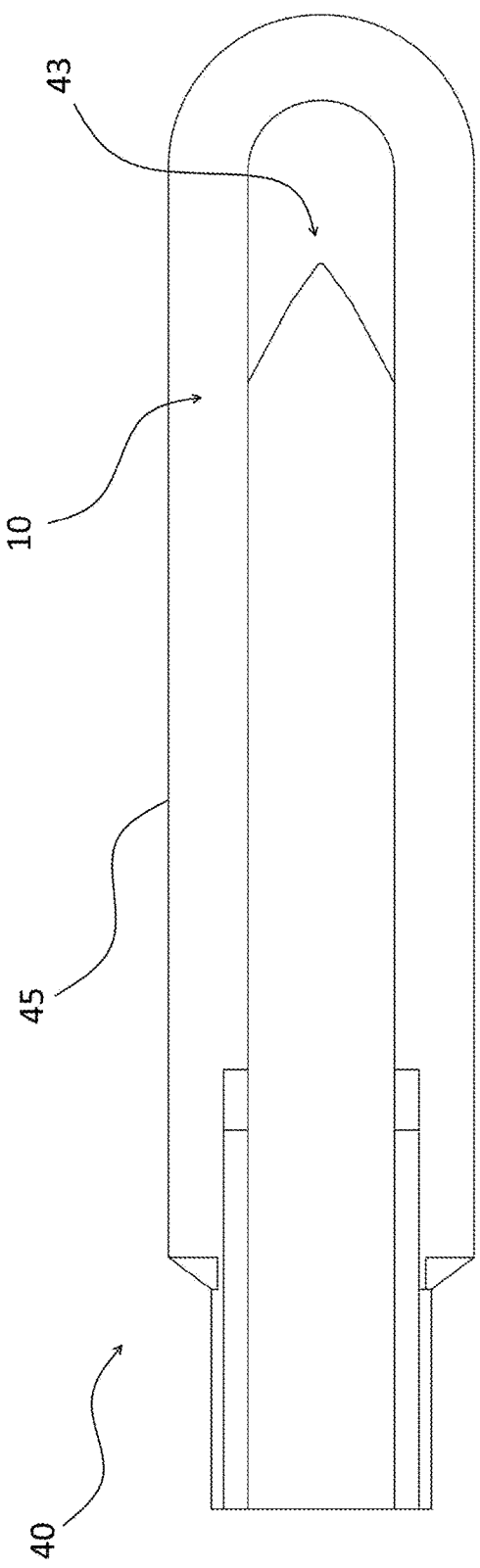
In FIG. 4b, a fiber probe which emits double ring radiation for laser ablation and which's tip is also flattened (truncated) in certain ratio for counter strike is shown.

An example of a laser ablation device is shown in FIGS. 4a and 4b. The laser ablation device can treat the natural diseases like venous insufficiency, of subsequently-formed diseases like fistula or of hemorrhoids formed as damaging of vein in short distance and etc. without leaving permanent damage and scar, thanks to its different optical fiber tips (40). For example, thanks to the truncated fiber tip (43) of optical fiber probe (40) shown in FIG. 4b, it is possible to use the laser beam as counter strike at a certain energy level in addition to the lateral strike. This counter-strike laser beam, or in other words guiding the incoming laser beam from fiber core center to directly counter side provides a significant advantage in the treatment of hemorrhoids. Since the specialist physician performs the operation by seeing in hemorrhoid treatment unlike endovenous laser ablation, specialist can direct the light in the desired direction. Because, unlike varicose veins, the hemorrhoids region is an apparent area, and in some cases, physicians may prefer to treat the tissue from the outside, instead of placing the probe (40) into the tissue to ablate.

As shown in FIGS. 4a and 4b, after the optical fiber probe (40) of the invention is produced, the fiber tip (10) is placed in a quartz glass body (45) which is closed by heat treatment. This process is intended to prevent the probe (40) from contact with the environment outside and has no effect on the optical properties of the probe (40).

The fiber end geometry parameters affecting the physical properties of the laser beams obtained by the present fiber probe (40) are shown in FIG. 5. The distances shown here; the vertical distance between the first section start and the fiber axis (a) and the vertical distance between the second section start and the fiber axis (b) are effective for the power distributions between the laser rings.

Similarly, there is an effect on the positions and power ratios of the laser beams formed in the distance between the first and second section (x) and the distance between the second section and the fiber tip (y) shown in FIG. 5. Furthermore, as shown in FIGS. 7a and 7b, the angles between the fiber axis (20) and the end portions of the first section (14) and the second section (15); namely in the first angle ($\theta$) and the second angle ($\alpha$), the positions of the inner and outer rings, consequently their diameters change.

Figures 6A, 6B, 6C:
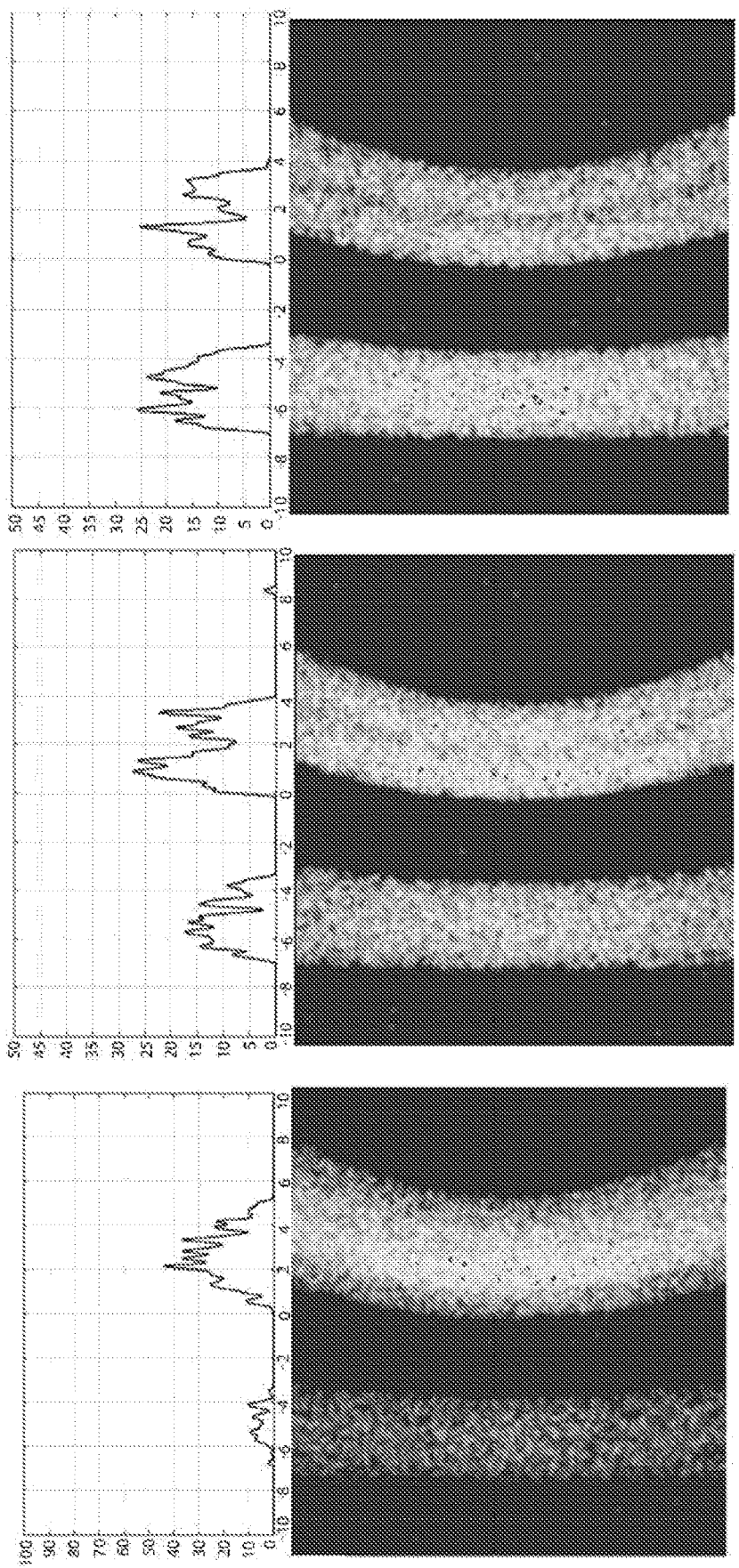
In FIGS. 6a, b and c, the beam power variations obtained according to the change in distance indicated by 'a' are depicted.
In FIG. 6b, the beam powers are shown for a=180.
In FIG. 6c, beam powers are presented for a=220.

The beam power variations obtained according to the parameter variation of the vertical distance between the first section start and the fiber axis (a) that is shown in FIG. 5 are shown in FIGS. 6a, 6b and 6c. Power differences of the double ring beams to each other for a=100 μm are shown in FIG. 6a, the beam powers for a=180 μm are shown in FIG. 6b and the beam powers for a=220 μm are shown in FIG. 6c.

Figure 7A:
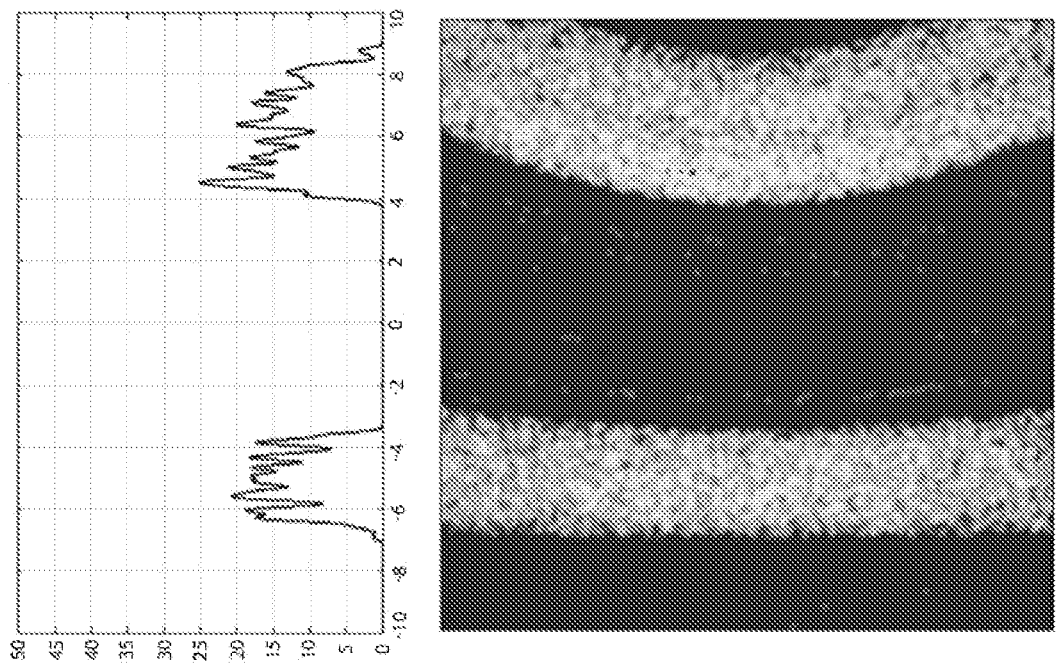
In FIGS. 7a and b, the changes in beam powers and ring diameters according to parameter changes in angle θ and α are shown for a=180.
Figure 7B:
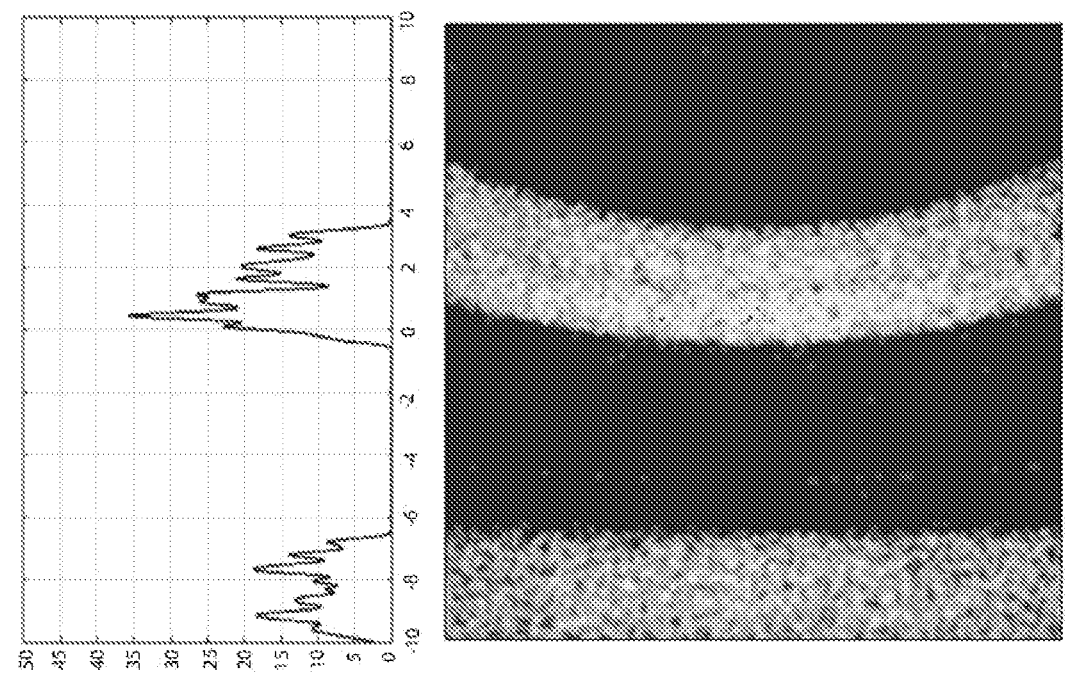
In FIG. 7b, it is shown that the outer ring diameter increases with the increase of the angle α, in other words, it moves outward away from the inner ring.

In FIGS. 7a and 7b, the changes in beam forces and ring diameters according to the first angle ($\theta$) and second angle ($\alpha$) parameter changes in the case where the vertical distance between the first section start and the fiber axis (a) in FIG. 5 is determined as 180.

The measurement results indicating that the diameter of the outer ring increases with the increase of the second angle ($\alpha$), in other words, the outer ring moves away from the inner ring are shown in FIG. 7b while the laser forces in the case where the inner ring diameter decreases with the decrease of the first angle ($\theta$), in other words, where the inner ring is moved away from the outer ring are presented in FIG. 7a. In order to obtain the optimal double ring laser powers for the treatment of the present double ring laser probe (40), the ranges of $\theta=20°-30°$, $\alpha=30°-40°$ were determined for the angle parameters.

The invention claimed is:

1. A laser ablation device for treatment of disease, the laser ablation device comprising: a fiber probe
    having a fiber with two different conical angled surfaces at a fiber tip, the fiber tip having a first conical shaped end formed at a first specific angle and a second conical shaped end formed at a second specific angle starting from a portion of the first conical shaped end, said fiber probe adapted to guide a beam of light inside the fiber so as to be reflected at the fiber tip, wherein the first and second conical shaped ends comprise a first section defining the first specific angle and a second section defining the second specific angle and relative to a longitudinal axis of the fiber, wherein the first section is adapted to cause a portion of the beam of light to reflect with a first reflection angle and to refract with a first refraction angle so as to form a first ring around the fiber tip, wherein the second section is adapted to cause another portion of the beam of light adjacent the longitudinal axis of the fiber to reflect with a second reflection angle and refract with a second refraction angle so as to form a second ring around the fiber tip.

2. The laser ablation device of claim 1, further comprising:
    a quartz glass body in which the fiber tip is placed.

* * * * *